United States Patent
Kurosawa et al.

(10) Patent No.: US 9,335,278 B2
(45) Date of Patent: May 10, 2016

(54) INSPECTION EQUIPMENT FOR SCREW PART OF BOTTLE-CAN

(75) Inventors: Akio Kurosawa, Neyagawa (JP); Tadayuki Sota, Neyagawa (JP)

(73) Assignees: Kurashiki Boseki Kabushiki Kaisha, Kurashiki-shi (JP); Universal Can Corporation, Tokyo (JP)

( * ) Notice: Subject to any disclaimer, the term of this patent is extended or adjusted under 35 U.S.C. 154(b) by 335 days.

(21) Appl. No.: 14/124,001

(22) PCT Filed: Jun. 4, 2012

(86) PCT No.: PCT/JP2012/064411
§ 371 (c)(1),
(2), (4) Date: Dec. 5, 2013

(87) PCT Pub. No.: WO2012/169472
PCT Pub. Date: Dec. 13, 2012

(65) Prior Publication Data
US 2014/0125793 A1 May 8, 2014

(30) Foreign Application Priority Data
Jun. 6, 2011 (JP) ................................. 2011-126218

(51) Int. Cl.
*H04N 9/47* (2006.01)
*G01N 21/95* (2006.01)
(Continued)

(52) U.S. Cl.
CPC ........ *G01N 21/9515* (2013.01); *G01B 11/2425* (2013.01); *G01B 11/25* (2013.01); *G01N 21/909* (2013.01); *G01N 21/9054* (2013.01); *G06T 7/0008* (2013.01)

(58) Field of Classification Search
CPC ...... G11B 27/034; G11B 27/105; H04N 5/76; H04N 5/765; H04N 5/85; H04N 5/907; H04N 5/775; H04N 5/781; H04N 21/47217; H04N 9/7921; H04N 9/8042; H04N 9/8205
USPC .......................... 348/92, 86, 94, 95; 386/200
See application file for complete search history.

(56) References Cited

U.S. PATENT DOCUMENTS 6,072,575 A * 6/2000 Loll ................... G01N 21/9054
356/239.1
6,104,482 A 8/2000 Brower et al.
2006/0000968 A1 1/2006 Katayama et al.

FOREIGN PATENT DOCUMENTS

CN 1299050 A 6/2001
DE 19920007 C1 7/2000
(Continued)

OTHER PUBLICATIONS

Office Action dated Aug. 27, 2015, issued for the Chinese patent application No. 201280028005.4.
(Continued)

*Primary Examiner* — Robert Chevalier
(74) *Attorney, Agent, or Firm* — Locke Lord LLP

(57) ABSTRACT

Inspection equipment for a screw part of a bottle-can having a mouth section provided with a curl portion in which an opening edge thereof is rolled up outward and the screw part for fitting a cap by threads below the curl portion for attaching the cap with a liner, the inspection equipment inspects a shape of the screw part of the mouth section by imaging an imaging area which is set so as to include a part of the mouth section while rotating the bottle-can around a can-axis, the inspection equipment including: a rotating device which holds and rotates the bottle-can around the can-axis; a thread-illumination device which irradiates illumination light toward the screw part of the bottle-can; an imaging device which continuously obtains inspection images including reflected light of the illumination light at the imaging area; and an thread-inspection device which inspects the screw part.

4 Claims, 6 Drawing Sheets

(51) Int. Cl.
*G01N 21/90* (2006.01)
*G01B 11/24* (2006.01)
*G01B 11/25* (2006.01)
*G06T 7/00* (2006.01)

(56) References Cited

FOREIGN PATENT DOCUMENTS

| JP | 2003-194532 A | 7/2003 |
| JP | 2003-254720 A | 9/2003 |
| JP | 2003-262507 A | 9/2003 |
| JP | 2003-262511 A | 9/2003 |

OTHER PUBLICATIONS

Supplementary European Search Report dated Oct. 7, 2014, issued for the European patent application No. 12797187.7.
International Search Report dated Aug. 14, 2012, issued for PCT/JP2012/064411.

\* cited by examiner (a)

(b)

INSPECTION EQUIPMENT FOR SCREW PART OF BOTTLE-CAN

CROSS REFERENCE TO RELATED APPLICATIONS

This application is related to two co-pending applications: "INSPECTION EQUIPMENT FOR MOUTH SECTION OF BOTTLE-CAN" filed even date herewith in the names of Akio Kurosawa and Tadayuki Sota as a national phase entry of PCT/JP2012/064409 and "INSPECTION METHOD AND INSPECTION EQUIPMENT FOR MOUTH SECTION OF BOTTLE-CAN" filed even date herewith in the names of Akio Kurosawa, Tadayuki Sota and Tadafumi Hirano as a national phase entry of PCT/JP2012/064410; which applications are assigned to the assignee of the present application and all incorporated by reference herein.

BACKGROUND OF THE INVENTION

1. Field of the Invention

The present invention relates to inspection equipment for a screw part of a bottle-can.

Priority is claimed on Japanese Patent Application No. 2011-126218, filed Jun. 6, 2011, the content of which is incorporated herein by reference.

2. Description of the Related Art

A can having a bottle-shape of aluminum alloy in which a cap is screwed on a mouth section having a screw is known as a container filled with contents such as drinks. The bottle-can is manufactured by forming an aluminum alloy sheet into a closed-end cylindrical body which has a bottom plate and a cylindrical side surface in one piece by performing drawing processing and ironing processing (i.e., DI forming); coating an inner surface and an outer surface of the close-ended cylindrical body; forming a shoulder and the mouth section by performing so-called neck-in processing on an opening portion; and performing screw-forming processing, curl-forming processing and the like on the mouth section.

A cap which is attached on the bottle-can is formed to have a peripheral wall with a straight cylindrical shape in a prior state to an attachment on the bottle-can. After placing the cap on a mouth section of the bottle-can, by deforming the cap so as to follow a screw part formed on the mouth section, a screw part is formed on the cap and the bottle-can is sealed with the cap. Accordingly, the shape of the screw part of the bottle-can decides the screw part of the cap which is attached subsequently.

Therefore, for a steady cap-openability, it is important for the screw part of the bottle-can that, for example: a position of a thread-starting part and a position of a thread-ending part are precise, a lead angle of the screw part is constant, and there is no deformation such as a bend or the like and linearity is excellent. Furthermore, it is required that the bottle-cans having a defect on the above properties are reliably eliminated as defective products by detecting in an inspection process.

As an inspection method for the screw part of the bottle-can, for example, Patent Document 1 discloses a method by: catching an outline of the bottle-can from an image of the bottle-can by illuminating from a rear, setting a top surface of an aperture section as a standard measuring-line based on the outline, and measuring dimensions of parts of a bottle-can based on the standard measuring-line.

Patent Document 2 discloses that: a thread-starting part of a bottle-can is colored beforehand so that a circumferential position of the bottle-can is specified by detecting the thread-starting part, and then parts of the bottle-can are measured from an outline image by measuring equipment disclosed in Patent Document 1.

Patent Document 3 discloses that: imaging an outline image of a bottle-can while rotating the bottle-can, tracking a measuring area with respect to a movement of a point of a thread ridge which moves along with the rotation, and obtaining position coordinates of the point of the thread ridge in the measuring area each at the rotation.

PRIOR ART DOCUMENT

Patent Document

[Patent Document 1] Japanese Unexamined Patent Application, First Publication No. 2003-254720
[Patent Document 2] Japanese Unexamined Patent Application, First Publication No. 2003-262507
[Patent Document 3] Japanese Unexamined Patent Application, First Publication No. 2003-262511

SUMMARY OF THE INVENTION

Problems to be Solved by the Invention

In the Patent Documents, the shape of the screw part is specified based on the outline image (a silhouette image) of the bottle-can, so that it is necessary to inspect by obtaining information of cross sections continuously. Accordingly, process is complicated and takes time. Furthermore, it is difficult to detect deformation such as a bend of the thread. It is troublesome to color the thread-starting part as disclosed in Patent Document 2 since the other process is necessitated.

The present invention is achieved in consideration of the above circumstances, and has an object to provide inspection equipment for a screw part of a bottle-can which can inspect the screw part of the bottle-can precisely in a short time.

Means for Solving the Problem

Inspection equipment for screw part of bottle-can according to the present invention is: inspection equipment for screw part of bottle-can having a mouth section provided with a curl portion in which an opening edge thereof is rolled up outward and the screw part for fitting a cap by threads below the curl portion for attaching the cap with a liner, the inspection equipment inspecting a shape of the screw part of the mouth section by imaging an imaging area which is set so as to include a part of the mouth section while rotating the bottle-can around a can-axis, the inspection equipment including: a rotating device which holds and rotates the bottle-can around the can-axis; a thread-illumination device which irradiates illumination light toward the screw part of the bottle-can in the imaging area diagonally upward from a radially outside and can-axially lower part; an imaging device which continuously obtains inspection images including reflected light of the illumination light at the imaging area; and an thread-inspection device which inspects the screw part including a thread-starting part by detecting the thread-starting part of the screw part based on an imaging result of the reflected light.

In the present inspection equipment, by irradiating the illumination light to the screw part from diagonally below, the illumination light is mainly reflected at an inclined surface of lower part than a ridgeline of a screw. The screw part of the bottle-can is formed from a thread-starting part at an upper end to a thread-ending part at a lower end, so that the lower inclined surface than the ridge line of the screw is formed so as to have a larger angle than a upper inclined surface than the ridge line of the screw with respect to the can-axis, and width thereof along the can-axis is small. Accordingly, by the reflected light of the illumination light which is irradiated to the lower inclined surface than the ridgeline, the inclined surface is imaged so as to emphasize the inclined surface, so that an upper edge thereof is clearly confirmed as the ridgeline of the screw. Therefore, it is found that one of the ends of the upper edge is the thread-starting part, and the other is the thread-ending part. Consequently, a position of the thread-starting part can be correctly detected, so that the screw part including the thread-starting part can be reliably inspected in a short time.

In the inspection equipment of the present invention, it is preferable that a carl portion-illumination device which irradiates illumination light toward the curl portion of the bottle-can in the imaging area downward from a can-axially upper part be further provided, the imaging device obtain the inspection image including two reflected lights of both the illumination devices in the imaging area; and the thread-inspection device have a function of specifying a reference position of the inspection image based on a imaging result of the reflected light of the cad portion-illumination device, and detects the thread-starting part of the screw part based on the imaging result of the reflected light of the thread-illumination device with respect to the reference position.

In the inspection equipment of screw part, the imaging device images both of the reflected lights of the two illumination device, so that the inspection image includes the screw part by the thread-illumination device and a top surface of the curl portion by the curl portion-illumination device. The top surface of the curl portion is: a position at an opening end of the bottle-can; a surface which is sealed by abutting the liner of the cap, formed at right angle to the can-axis; and a part which is usually not displaced largely even though the bottle-can is rotated around the can-axis. Accordingly, by detecting the thread-starting part referring the position of the top surface of the curl portion, it is possible to detect the thread-starting part correctly and inspect the screw part.

If the position of the top surface by the reflected light from the curl portion is displaced largely in the inspection image, it can be deemed that a dimple or the like is formed on the top surface of the curl portion. Therefore, it is also possible to inspect presence of a defect on the curl portion.

The curl portion-illumination device may irradiate the illumination light to the mouth section simultaneously with the thread-illumination device, or may alternately irradiate the illumination light by flickering as follows.

Specifically, in the inspection equipment for screw part of bottle-can of the present invention, it is possible that: the thread-illumination device and the carl portion-illumination device alternately irradiate the illumination lights by flickering, and the thread-inspection device has a function of separating the inspection image including the reflected light which is obtained by the imaging device in timing with the flickering of the illumination lights into an inspection image including the reflected light of the curl portion-illumination device and an inspection image including the reflected light of the thread-illumination device.

By separating the inspection images by flickering alternately, mutual interference between the two reflected lights can be prevented. Accordingly, the imaging results of the reflected lights can be clearly indicated in the inspection images, and inspection precision can be improved.

In the inspection equipment for screw part of bottle-can of the present invention, it is preferable that the thread-illumination device irradiate the illumination light at an inclined angle of 15° to 80° with respect to the can-axis.

By irradiating at the above inclined angle, it is possible to emphasize the reflected light from the screw part of the bottle-can at the lower inclined surface than the ridgeline of the screw in particular.

Effects of the Invention

According to the inspection equipment for screw part of bottle-can of the present invention, by irradiating the reflected light of the illumination light from diagonally below of the screw part, the lower inclined surface than the ridgeline of the screw is imaged with emphasis and the upper edge thereof is clearly confirmed as the ridgeline of the screw. Therefore, it is possible to correctly and instantly detect the position of the thread-starting part, so that the screw part can be inspected in a short time.

DETAILED DESCRIPTION OF THE INVENTION

Below, embodiments of inspection equipment for screw part of bottle-can according to the present invention will be explained with reference to drawings.

Figure 1:
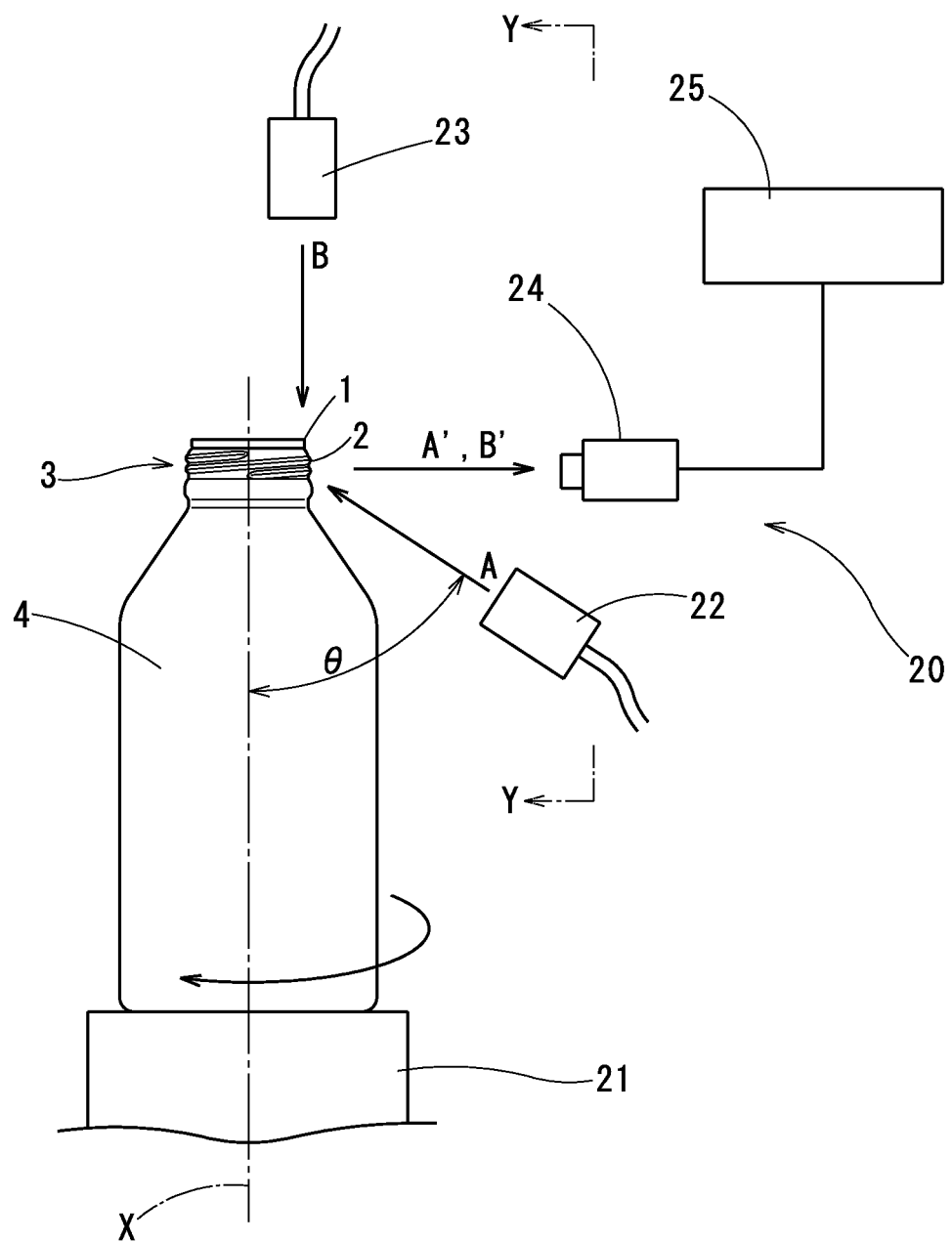
FIG. 1 It is a front view showing an embodiment of inspection equipment for screw part of bottle-can according to the present invention.
Figure 2:
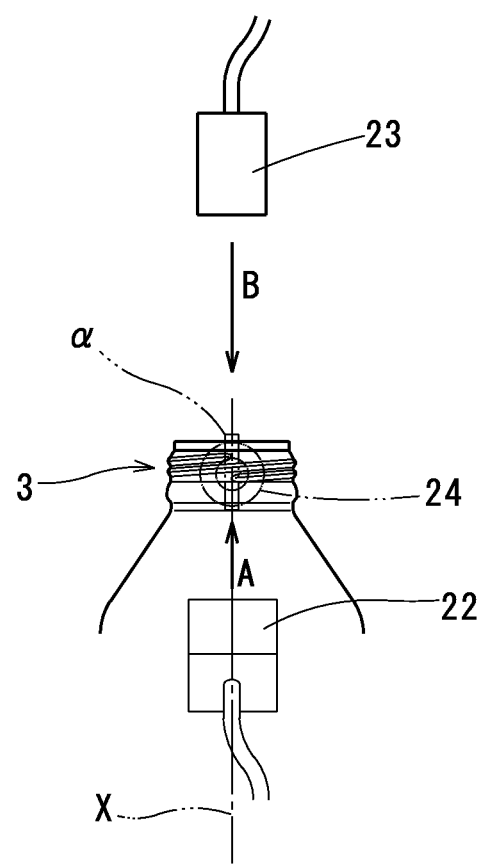
FIG. 2 It is a side view in which a part is omitted, taken along the Y-Y line in FIG. 1.
Figure 3:
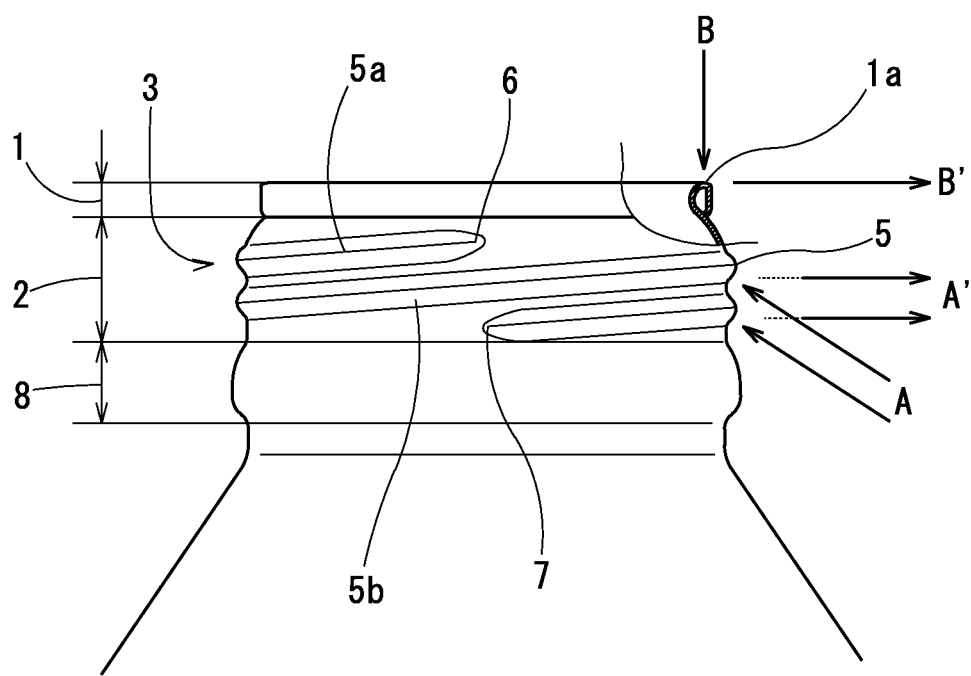
FIG. 3 It is a front view in which a part is shown in a cross section, showing a relationship between a mouth section of a bottle-can and illumination light in the inspection equipment in FIG 1.

Inspection equipment 20 for screw part of bottle-can (hereinafter, "inspection equipment") of the present invention is, as shown in FIG. 1 to FIG. 3, with respect to a bottle-can 4 having a cylindrical mouth section 3 provided with a curl portion 1 in which an opening edge thereof is rolled up outward and the screw part 2 for fitting a cap by threads below the curl portion 1 for attaching the cap with a liner (not illustrated), equipment for inspecting a shape of the screw part 2 by imaging an imaging area α which is set so as to include a part of the curl portion 1 and the screw part 2. In the screw part 2, one thread ridge 5 is formed for 1.8 turns to 2.2 turns, for example, an upper end thereof is set as a thread-starting part 6 and a lower end thereof is set as a thread-ending part 7. The mouth section 3 in the bottle-can 4 is a part including the curl portion 1, the screw part 2 and a jaw part 8 for locking a lower end of the cap below the screw part 2. In the screw part 2, a streak protruding radially outward is the thread ridge 5.

The inspection equipment 20 is provided with: a rotating device 21 which holds the bottle-can 4 by vacuum suction or the like and rotates the bottle-can 4 around a can-axis X; a thread-illumination device 22 which irradiates illumination light A so as to cover the screw part 2 of the bottle-can 4 in the imaging area α; a curl portion-illumination device 23 which irradiates illumination light B so as to cover the curl portion 1 of the bottle-can 4 in the imaging area α; an imaging device 24 which continuously obtains inspection images including reflected lights A' and B' of the illumination lights A and B from the illumination devices 22 and 23 at the imaging area α; and a thread-inspection device 25 which detects the thread-starting part 6 of the screw part 2 based on the inspection images obtained by the imaging device 24 and inspects the shape of the screw part 2 referring the thread-starting part 6.

In the inspection equipment 20, as aforementioned, the imaging area α is set so as to cover the entire mouth section 3 from a highest end of a top surface 1a of the curl portion 1 to a lower end of the jaw part 8 including the screw part 2. The thread-illumination device 22 irradiates the illumination light A to an area covering the imaging area α in the screw part 2; and the curl portion-illumination device 23 irradiates the illumination light B to an area covering the imaging area it in the top surface 1a of the curl portion 1.

In this case, the thread-illumination device 22 is disposed radially outside the screw part 2 and below the screw part 2 in the can-axis X direction so as to illuminate an inclined surface 5b which is disposed lower than a ridgeline 5a of the thread ridge 5 and illuminate the lower inclined surface 5b than the ridgeline 5a of the thread ridge 5 from diagonally below. Specifically, the thread-illumination device 22 is disposed so that an optical axis of the illumination light A which is irradiated from the thread-illumination device 22 has an inclined angle θ of 15° to 80° with respect to the can-axis X.

The curl portion-illumination device 23 is disposed above the curl portion 1 of the bottle-can 4 in the can-axis X direction and illuminates the top surface 1a downward along the can-axis X direction.

The imaging device 24 continuously images the linear imaging area α by a line sensor camera and sets the imaging area α linearly along the can-axis X so as to include the entire mouth section 3 from the highest end of the top surface 1a of the curl portion 1 and the screw part 2 to the lower end of the jaw part 8. The inspection image is obtained as a monochrome picture having a high-brightness part by the reflected light of the illumination lights from the illumination devices 22 and 23 and a low-brightness part surrounding the high-brightness part.

With respect to the illumination devices 22 and 23 and the imaging device 24, by rotating the bottle-can 4 around the can-axis X by the rotating device 21, the whole circumference of the mouth section 3 is scanned, and the inspection images including the reflected lights A' and B' in the imaging area α are continuously imaged. The inspection images are inputted to the thread-inspection device 25 which is connected with the imaging device 24 and utilized for the inspection of the shape of the screw part.

Figure 4:
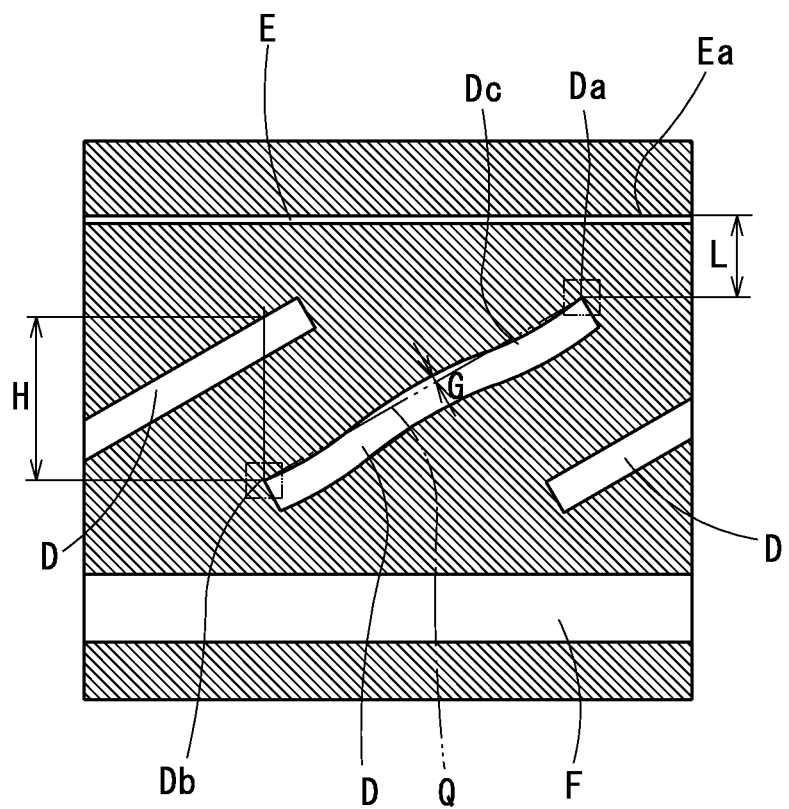
FIG. 4 It is a view showing an inspection image which is imaged in the inspection equipment in FIG. 1.

In the inspection equipment 20 as configured above, as shown in FIG. 4, in the inspection image obtained by the imaging device 24, both an image D of the inclined surface 5b of the thread ridge 5 by the reflected light A' of the illumination light A from the thread-illumination device 22 and an image E of the top surface 1a of the curl portion 1 by the reflected light B' of the illumination light B from the curl portion-illumination device 23 are included. The vertical direction of FIG. 4 is along the can-axis X direction.

When inspecting the screw part from the inspection image, a reference position of the inspection image is specified based on the imaging result of the reflected lights A' and B', and then the thread-starting part 6 is specified from the reference position.

In the image E of the top surface 1a of the curl portion 1, the top end Ea thereof indicates the highest end of the top surface 1a. The top end Ea is set as the reference position. An end part Da of the image D of the thread ridge 5 existing in an area which is away at a prescribed distance L from the reference position along the can-axis X is detected. If the end part Da is detected, it is set as a position of the thread-starting part 6. The end part of the thread ridge 5 can be recognized by a figure of a boundary (e.g., hooked "L" shape) between the high-brightness part and the low-brightness part by the reflected light in the inspection image.

Next, the thread-ending part 7 is specified by an end part Db of the image D of the thread ridge 5 in an area at a position of a prescribed length and a prescribed lead angle from the end part Da corresponding to the thread-starting part. The thread-starting part 6 and the thread-ending part 7 are specified by obtaining the image D of the thread ridge 5 from the reflected light at the lower inclined surface 5b than the ridgeline 5a, so that an upper edge Dc of the image D indicates the ridgeline 5a of the thread ridge 5. Accordingly, by detecting the positions of both the end parts Da and Db of the upper edge Dc of the image D, it is possible to specify the positions of the thread-starting part 6 and the thread-ending part 7 on the ridgeline 5a of the thread ridge 5.

With respect to a straight line Q which links the end parts Da and Db corresponding to the thread-starting part 6 and the thread-ending part 7, a bend of the thread ridge 5 is detected by tracing a displacement of the upper edge Dc of the thread ridge 5 in the image D. (In FIG. 4, the center image D is indicated so as to emphasize a bend thereof; and a o largest displacement is denoted by a reference symbol G.) From a separated distance H along the can-axis between the adjacent image D of the thread ridge (it means that a plurality of the thread ridges are sighted because of the rotation of the bottle-can), for example, from the separated distance H along the can-axis between the one end part Db and the top edge Dc of the image D of the thread ridge which is sighted above the end part Db, a screw pitch is as calculated.

As described above, by the inspection equipment 20 for screw part: the reference position of the inspection image is specified from the reflected light B' of the illumination light B from the curl portion-illumination device 23 which illuminates the top surface 1a of the curl portion 1; the position of the thread-starting part 6 of the screw part 2 is specified from the reference position; then the shape of the screw part 2 (i.e., the screw pitch, the bend of the screw and the like) is inspected. Therefore, the shape of the screw part 2 can be correctly inspected by specifying the correct position of the thread-starting part 6.

Moreover, since the bottle-can 4 is rotated around the can-axis X while being imaged, the whole circumference of the curl portion 1 can be scanned by the reflected light B' of the illumination light B from the curl portion-illumination device 21 Normally, the image E of the top surface 1a of the curl portion 1 is recognized as a straight line as shown in FIG. 4. However, if a dimple is on the top surface 1a of the curl portion 1, the image E of the top surface 1a is displaced up and down of the drawing. Accordingly, by tracing the image E of the top surface 1a, the displacement exceeding a prescribed value can be found as a defect of the curl portion 1.

In FIG. 4, the reference symbol F denotes an image of the jaw part 8.

In the above embodiment, both the thread-illumination device 22 and the curl portion-illumination device 23 illuminate the screw part 2 and the top surface 1a of the curl portion 1, and both the reflected lights A' and B' are imaged. However, it is approved to make the thread-illumination device 22 and the curl portion-illumination device 23 flicker is alternately so as to image the reflected lights A' and B' continuously and alternately.

Figure 5A:
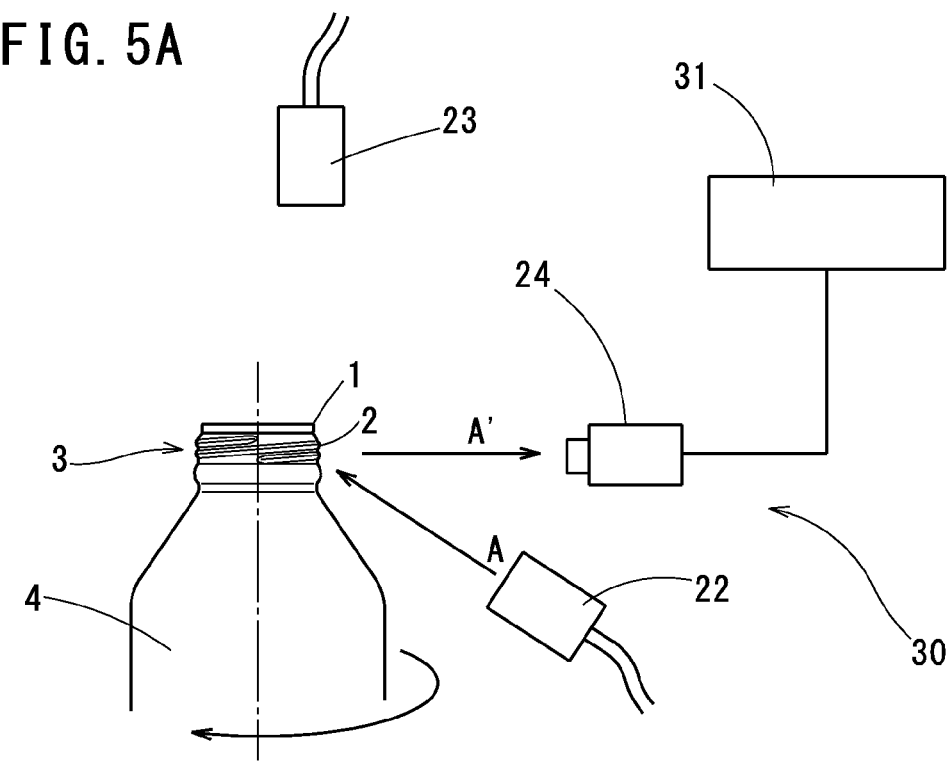
FIG. 5A It is a front view in which a part is omitted, showing a state in which reflected light of illumination light from a thread-illumination device is imaged in another embodiment of inspection equipment for screw part of bottle-can according to the present invention.
Figure 5B:
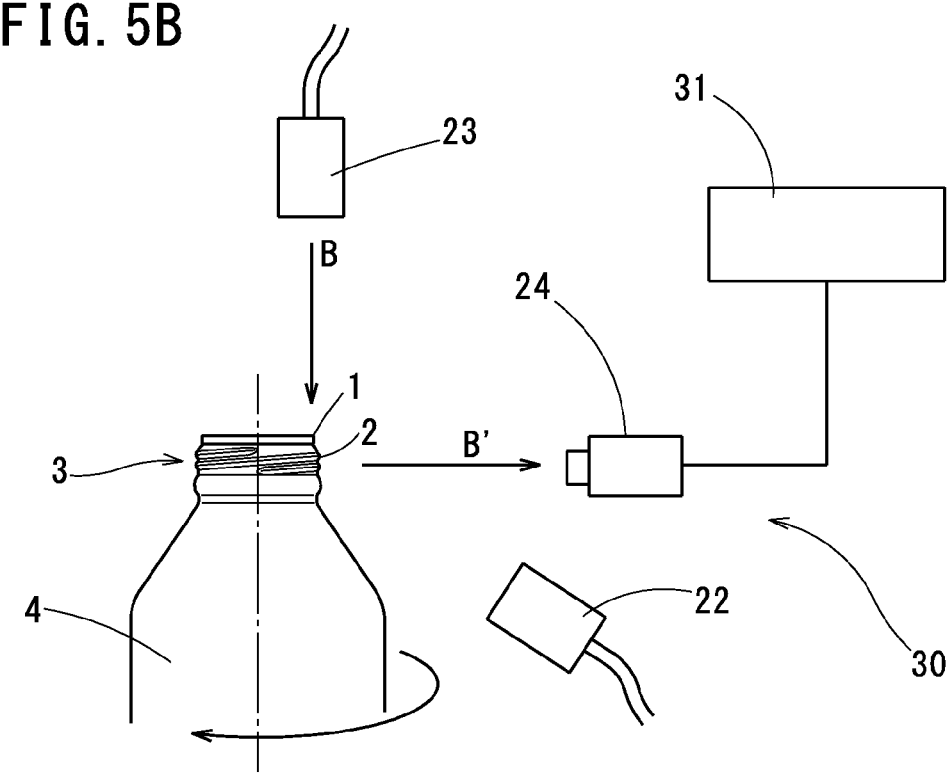
FIG. 5B It is a front view in which a part is omitted, showing a state in which reflected light of illumination light from a curl portion-illumination device is imaged in another embodiment of inspection equipment for screw part of bottle-can according to the present invention.

That is to say, in inspection equipment 30 for screw part of another embodiment shown in FIG. 5A and FIG. 5B, the illumination devices and 23 are flickered at a frequency of 60 Hz for example, and the reflected lights A' and B' of the illumination lights A and B are imaged continuously and alternately by the imaging device 24 of the line sensor camera, so that an image is obtained in a state in which the reflected light A' of the illumination light A from the thread-illumination device 22 and the reflected light B' of the illumination light B from the curl portion-illumination device 23 are alternated. By separating this image to two images in timing with the flicker by computer processing, the reflected light A' of the illumination light A from the thread-illumination device 22 and the reflected light B' of the illumination light B from the curl portion-illumination device 23 can be extracted individually.

Figure 6:
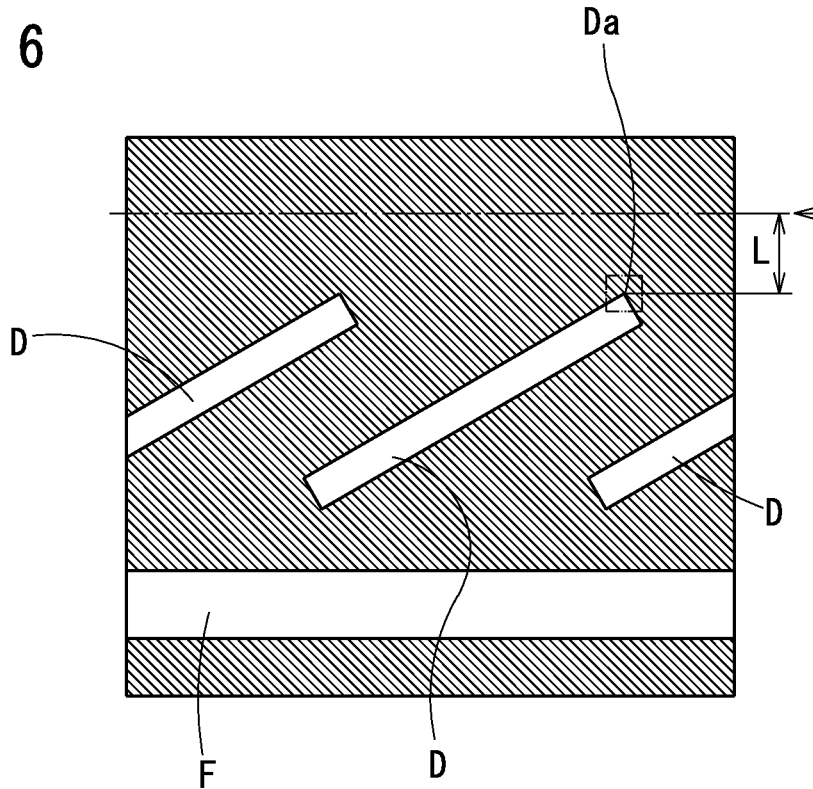
FIG. 6 It is an inspection image which is imaged in the embodiment of FIGS. 5A and 5B: the part (a) shows an image of reflected light from the thread-illumination device; and the part (b) shows an image of reflected light from the curl portion-illumination device.
Figure 6:
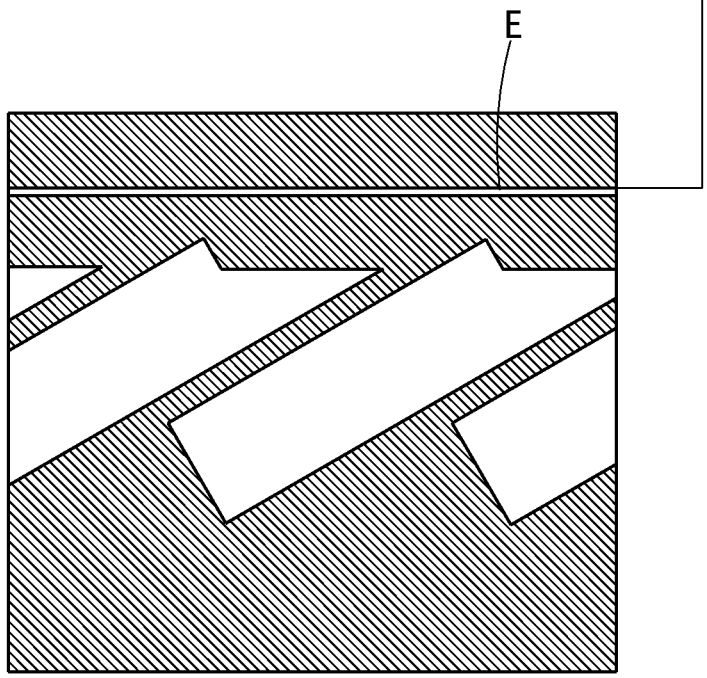

A part (a) in FIG. 6 shows an inspection image in which the reflected light A' of the illumination light A from the thread-illumination device 22 is mainly indicated. A part (b) in FIG. 6 shows an inspection image in which the reflected light B' of the illumination light B from the curl portion-illumination device 23 is mainly indicated. Those inspection images show a same position coordinate. Although it is not described clearly for concision in FIG. 4 and the description of the first embodiment, if the illumination light A from the thread-illumination device 22 and the illumination light B from the curl portion-illumination device 23 are simultaneously irradiated, an inspection image in which the part (a) in FIG. 6 and the part (b) in FIG. 6 are synthesized is obtained, so that the illumination light B from the curl portion-illumination device 23 interferes with the illumination light A irradiated to the screw part 2 from the thread-illumination device 22. Accordingly, both the reflected lights A' and B' are mixed in the image, so that an outline of the thread ridge 5 may be blurred as a whole in the image. On the other hand, if only the reflected light A' of the illumination light A from the thread-illumination device 22 is sighted, the illumination light B from the curl portion-illumination device 23 do not affect, so that the inclined surface 5b of the thread ridge 5 is clearly indicated.

By computer processing of a thread-inspection device 31 for an inspection image from the imaging device 24, the thread-starting part 6 is detected as follows. After separating into two inspection image shown in the part (a) in FIG. 6 and the part (b) in FIG. 6, in the inspection image shown in the part (b) in FIG. 6, recognizing the image E of the curl portion 1 from an imaging result of the reflected light B' of the illumination light B from the curl portion-illumination device 23, detecting coordinates of a highest end of the top surface 1a, and a position coordinate in the inspection image of the part (a) in FIG, 6 corresponding to this position coordinate is calculated. Then, referring the position coordinate, from the imaging result of the reflected light A' of the illumination light A from the thread-illumination device 22, detecting the end part Da of the image D of the thread ridge 5 existing in an area which is away at a prescribed distance L along the can-axis X.

In a case in which the end part Da is detected, it is set as a position of the thread-starting part 6.

In addition, it is possible to specify the thread-ending part 7, detect the bend of the thread ridge 5 or the like by the same method as that of the above-mentioned embodiment.

The present invention is not limited to the above-described embodiments and various modifications may be made without departing from the scope of the present invention,

INDUSTRIAL APPLICABILITY

To provide inspection equipment for screw part of bottle-can which can inspect the screw part of the bottle-can correctly in a short time.

DESCRIPTION OF REFERENCE SYMBOLS 1 curl portion
1a top surface
2 screw part
3 mouth section
4 bottle-can
5 thread ridge
5a ridgeline
5b inclined surface
6 thread-starting part
7 thread-ending part
20 inspection equipment for screw part
21 rotating device
22 thread-illumination device
23 curl portion-illumination device
24 imaging device
25 thread-inspection device
30 inspection equipment for screw part
31 thread-inspection device
α imaging area
A, B illumination light
A', B' reflected light

The invention claimed is:

1. Inspection equipment for screw part of bottle-can having a mouth section provided with a curl portion in which an opening edge thereof is rolled up outward and the screw part for fitting a cap by threads below the curl portion for attaching the cap with a liner, the inspection equipment inspecting a shape of the screw part of the mouth section by imaging an imaging area which is set so as to include a part of the mouth section while rotating the bottle-can around a can-axis, the inspection equipment comprising:
   a rotating device which holds and rotates the bottle-can around the can-axis;
   a thread-illumination device which irradiates illumination light toward the screw part of the bottle-can in the imaging area diagonally upward from a radially outside and can-axially lower part;
   an imaging device which continuously obtains inspection images including reflected light of the illumination light at the imaging area; and
   an thread-inspection device which inspects the screw part including a thread-starting part by detecting the thread-starting part of the screw part based on an imaging result of the reflected light.

2. The inspection equipment for screw part of bottle-can according to claim 1, further comprising a carl portion-illumination device which irradiates illumination light toward the curl portion of the bottle-can in the imaging area downward from a can-axially upper part, wherein:

the imaging device obtains the inspection image including two reflected lights of both the illumination devices in the imaging area; and the thread-inspection device has a function of specifying a reference position of the inspection image based on a imaging result of the reflected light of the carl portion-illumination device, and detects the thread-starting part of the screw part based on the imaging result of the reflected light of the thread-illumination device with respect to the reference position.

3. The inspection equipment for screw part of bottle-can according to claim 2, wherein: the thread-illumination device and the carl portion-illumination device alternately irradiate the illumination lights by flickering, and the thread-inspection device has a function of separating the inspection image including the reflected light which is obtained by the imaging device in timing with the flickering of the illumination lights into an inspection image including the reflected light of the curl portion-illumination device and an inspection image including the reflected light of the thread-illumination device.

4. The inspection equipment for screw part of bottle-can according to claim 1, wherein the thread-illumination device irradiates the illumination light at an inclined angle of 15° to 80° with respect to the can-axis.

* * * * *